US008715625B1

(12) United States Patent
Rokitowski et al.

(10) Patent No.: US 8,715,625 B1
(45) Date of Patent: May 6, 2014

(54) NATURAL ORAL CARE COMPOSITIONS

(75) Inventors: Karen Lee Rokitowski, Durham, NC (US); Amy Tracy Hart, Durham, NC (US); Celeste Anne Lutrario, Durham, NC (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 13/103,747

(22) Filed: May 9, 2011

Related U.S. Application Data

(60) Provisional application No. 61/333,073, filed on May 10, 2010.

(51) Int. Cl.
*A61Q 11/00* (2006.01)
*A61K 8/00* (2006.01)
*A61K 8/18* (2006.01)
*A61K 8/21* (2006.01)
*A61K 8/24* (2006.01)
*A61K 8/73* (2006.01)
*A61K 8/97* (2006.01)
*C03C 3/076* (2006.01)
*C03C 3/087* (2006.01)
*C03C 3/097* (2006.01)

(52) U.S. Cl.
USPC ............ 424/49; 424/52; 424/57; 424/58; 424/401; 501/55; 501/63; 501/70; 433/215; 433/216; 433/217.1

(58) Field of Classification Search
USPC ........ 424/49, 52, 57, 58, 401; 501/55, 63, 70; 433/215, 216, 217.1
See application file for complete search history.

(56) References Cited

U.S. PATENT DOCUMENTS

| 3,137,632 | A | 6/1964 | Schiraldi |
|---|---|---|---|
| 3,981,736 | A | 9/1976 | Broemer et al. |
| 4,254,101 | A | 3/1981 | Denny, Jr. |
| 4,806,339 | A | 2/1989 | Parran, Jr. et al. |
| 4,812,306 | A | 3/1989 | Cocherell et al. |
| 5,037,639 | A | 8/1991 | Tung |
| 5,074,916 | A | 12/1991 | Hench et al. |
| 5,089,255 | A | 2/1992 | Gaffar et al. |
| 5,192,531 | A | 3/1993 | Gaffar et al. |
| 5,268,167 | A | 12/1993 | Tung |
| 5,281,411 | A | 1/1994 | Majeti et al. |
| 5,294,434 | A | 3/1994 | King et al. |
| 5,318,929 | A | 6/1994 | Jana et al. |
| 5,424,059 | A | 6/1995 | Prencipe et al. |
| 5,455,024 | A | 10/1995 | Winston et al. |
| 5,603,920 | A | 2/1997 | Rice |
| 5,614,175 | A | 3/1997 | Winston et al. |
| 5,688,492 | A | 11/1997 | Galley et al. |
| 5,735,942 | A | 4/1998 | Litkowski et al. |
| 5,741,479 | A | 4/1998 | Masterman et al. |
| 5,833,954 | A | 11/1998 | Chow et al. |
| 5,874,066 | A | 2/1999 | Hack et al. |
| 5,891,233 | A | 4/1999 | Salonen et al. |
| 5,906,809 | A | 5/1999 | Hack et al. |
| 5,925,335 | A * | 7/1999 | Shuch et al. ............... 424/49 |
| 5,972,384 | A | 10/1999 | Thut et al. |
| 5,980,869 | A | 11/1999 | Sanker et al. |
| 5,981,412 | A | 11/1999 | Hench et al. |
| 5,993,786 | A | 11/1999 | Chow et al. |
| 6,054,119 | A | 4/2000 | Hurme et al. |
| 6,054,400 | A | 4/2000 | Brink et al. |
| 6,086,374 | A | 7/2000 | Litkowski et al. |
| 6,121,175 | A | 9/2000 | Drescher et al. |
| 6,190,643 | B1 | 2/2001 | Stoor et al. |
| 6,365,132 | B1 | 4/2002 | Litkowski et al. |
| 6,485,711 | B1 | 11/2002 | Olmstead |
| 6,495,168 | B2 | 12/2002 | West et al. |
| 6,517,863 | B1 | 2/2003 | LaTorre et al. |
| 6,565,873 | B1 * | 5/2003 | Shefer et al. ............... 424/426 |
| 6,706,256 | B2 | 3/2004 | Lawlor |
| 6,740,311 | B2 | 5/2004 | White, Jr. et al. |
| 6,986,906 | B2 | 1/2006 | Selzer et al. |
| 7,153,482 | B2 | 12/2006 | Noerenberg et al. |
| 7,182,937 | B2 * | 2/2007 | Xu et al. ............... 424/49 |
| 7,250,174 | B2 | 7/2007 | Lee et al. |
| 7,279,151 | B2 | 10/2007 | Pushpangadan et al. |
| 7,329,126 | B2 | 2/2008 | Cook et al. |
| 2002/0068039 | A1 | 6/2002 | Pan et al. |
| 2003/0147817 | A1 | 8/2003 | Deinas |
| 2005/0142077 | A1 * | 6/2005 | Zimmer et al. ............... 424/57 |
| 2006/0013402 | A1 | 1/2006 | Sutton et al. |

(Continued)

FOREIGN PATENT DOCUMENTS

| EP | 1333797 B1 | 8/2006 |
|---|---|---|
| EP | 1731132 B | 12/2008 |
| EP | 2059218 A | 5/2009 |
| EP | 2111853 A1 | 10/2009 |
| JP | 2006028152 | 2/2006 |
| JP | 2009155271 A | 7/2009 |
| KR | 20100039750 | 4/2010 |
| WO | WO2008023041 A1 | 2/2008 |
| WO | WO2008137009 A1 | 11/2008 |
| WO | WO2008137010 A1 | 11/2008 |
| WO | WO2009076491 | 6/2009 |
| WO | WO2010041073 | 4/2010 |
| WO | WO2010041884 | 4/2010 |
| WO | WO2010042754 | 4/2010 |

OTHER PUBLICATIONS

Burt's Bees, http://www.burtsbees.com/natural-products/toothpaste/natural-toothpaste-multicare-fluoride.html, Jan. 2010.*

Horton, A., Review of Sea Fresh Gel Toothpaste with Fluoride by Jason Natural Personal Care Products, http://voices.yahoo.com/review-sea-fresh-gel-toothpaste-fluoride-by-2492218.html?cat=69, Jan. 21, 2009.*

Epinions, Jason Natural Cosmetics Toothpaste Van Mint Power Smile 6 Oz, http://www.epinions.com/review/Jason_Toothpaste_Van_Mint_Power_Smile_6_oz/content_437124566660, pp. 1-2, Jul. 13, 2008.*

(Continued)

*Primary Examiner* — Lezah Roberts
(74) *Attorney, Agent, or Firm* — Ann Lee

(57) ABSTRACT

A natural anhydrous oral care composition with a limited number of naturally-derived, naturally processed, generally regarded as safe (GRAS) ingredients including an effective amount of a bioactive glass is described. The topical application of the composition to human teeth cleanses, remineralizes and reduces plaque build-up on teeth.

13 Claims, 1 Drawing Sheet

(56) References Cited

U.S. PATENT DOCUMENTS

| | | |
|---|---|---|
| 2006/0045851 A1 | 3/2006 | Fitzgerald et al. |
| 2006/0134025 A1 | 6/2006 | Trivedi et al. |
| 2006/0140883 A1 | 6/2006 | Trivedi et al. |
| 2006/0140884 A1 | 6/2006 | Worrell et al. |
| 2006/0141039 A1 | 6/2006 | Boyd et al. |
| 2006/0141073 A1 | 6/2006 | Worrell et al. |
| 2006/0188589 A1 | 8/2006 | Mezine et al. |
| 2006/0286044 A1 | 12/2006 | Robinson et al. |
| 2007/0110683 A1 | 5/2007 | Levine et al. |
| 2007/0166246 A1 | 7/2007 | Takagaki et al. |
| 2007/0264291 A1 | 11/2007 | Greenspan et al. |
| 2007/0275021 A1 | 11/2007 | Lee et al. |
| 2008/0031831 A1 | 2/2008 | Laai |
| 2008/0050407 A1 | 2/2008 | Haas |
| 2008/0095719 A1 | 4/2008 | Herrmann et al. |
| 2008/0138299 A1 | 6/2008 | Shi |
| 2008/0193557 A1 | 8/2008 | Reynolds |
| 2008/0241117 A1 | 10/2008 | Gaffar et al. |
| 2008/0274062 A1 | 11/2008 | Bergeron et al. |
| 2009/0010859 A1 | 1/2009 | Waterfield |
| 2009/0035226 A1 | 2/2009 | Tempesta et al. |
| 2009/0087501 A1 | 4/2009 | Cummins |
| 2009/0123395 A1 | 5/2009 | Behan et al. |
| 2009/0185987 A1 | 7/2009 | Mitra et al. |
| 2009/0208428 A1 | 8/2009 | Hill et al. |
| 2009/0317339 A1 | 12/2009 | Sharman et al. |
| 2009/0324516 A1 | 12/2009 | Muscle et al. |
| 2010/0086497 A1 | 4/2010 | Burwell et al. |
| 2010/0086618 A1 | 4/2010 | Pashley et al. |

OTHER PUBLICATIONS

Natural Products Association, http://www.naturalproductsassoc.org/site/PageServer?pagename=naturalstandard, Sep. 1, 2010, pp. 1-23.*

* cited by examiner

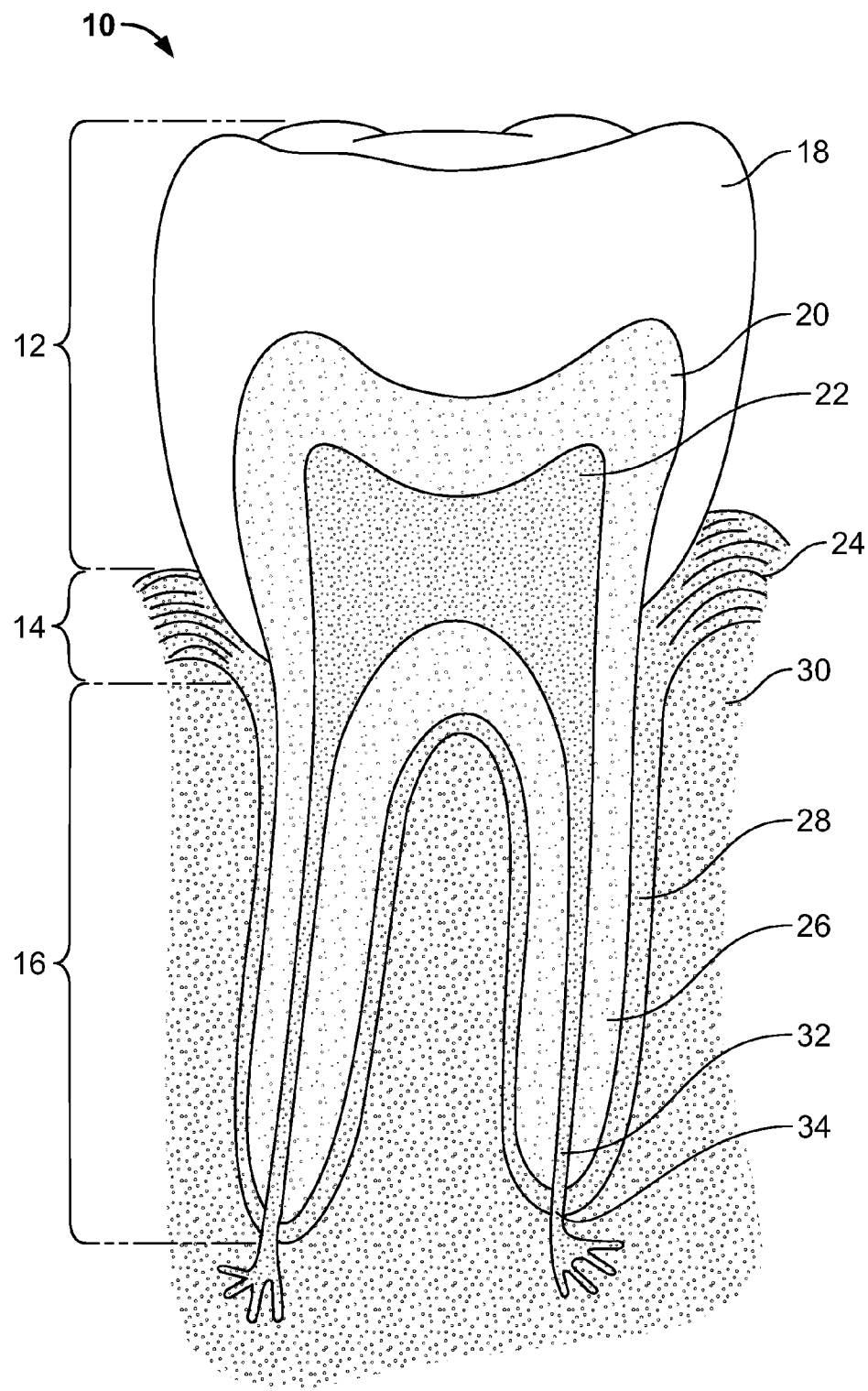

NATURAL ORAL CARE COMPOSITIONS

CROSS REFERENCES TO RELATED APPLICATIONS

This application claims the benefit of U.S. Provisional Application No. 61/333,073, filed May 10, 2010, which is hereby incorporated by reference in its entirety.

BACKGROUND OF THE INVENTION

1. Field of the Invention

The present invention relates generally to natural, anhydrous oral care compositions suitable for topical application for cleansing, remineralizing and reducing plaque build-up on human teeth. The compositions are produced from naturally-derived naturally-processed, GRAS ingredients and have good remineralizing and plaque-reduction properties.

2. Description of the Related Art

Oral care compositions have progressed and created a large chemical industry devoted to developing new synthetic compounds to achieve ever improving tooth health for the consumer.

Tooth hypersensitivity is a common problem which affects about tens of millions of adults in the United States. It is estimated that close to 20% of adults in the U.S. have at least one or more sensitive teeth. Hypersensitive teeth may be sensitive to cold, heat, air or sugary foods.

The incidence of tooth hypersensitivity increases with age. Tooth hypersensitivity is believed to be related to the general increase in exposed root surfaces of teeth as a result of periodontal disease, tooth brush abrasion, or cyclic loading fatigue of the thin enamel near the dento-enamel junction. When root surfaces are exposed, dentinal tubules are also exposed. Dentinal tubules are naturally present in the dentinal layer of the tooth and they provide for an osmotic flow between the inner pulp region of the tooth and the outer root surfaces.

It is well established that tooth decay, development of plaque, plaque build-up, gingivitis, periodontal disease and other conditions of the oral cavity are associated with pathogens such as *Actinobacillus actinomycetemcomitans, Porphyromonas gingivalis, Actinomyces naeslundii*, and/or *Streptococcus mutans*, among many others. For most individuals, proper oral care, including brushing with a standard, commercial dentifrice (such as a toothbrush) and appropriate toothbrushing along with the use of dental floss daily will maintain proper oral health. Even with proper oral health care, a significant number of persons suffer from tooth decay, plaque build-up and gingivitis that can lead to serious oral health issues.

It is estimated that over 150,000,000 cavities are filled in the United States every year at a cost of over $11 billion, and that over 20% of the adult population suffers from some form of gingivitis, from mild inflammation to severe gingival bleeding.

Gingivitis is a first form of periodontal disease typically caused by the long-term effects of plaque deposits. Plaque is the sticky, colorless, film material that develops on the exposed portions of the teeth. Unremoved plaque mineralizes into a hard deposit called calculus or tartar that becomes trapped at the base of the tooth. Plaque and calculus cause mechanical irritation and inflammation while bacteria in plaque cause the gums to become infected, swollen and tender. Other causes of gingivitis may include overly vigorous brushing or flossing the teeth or other injury or trauma to the gums. The conditions and problems stemming from plaque, plaque build-up and gingivitis may eventually lead to tooth loss, and a general degradation in a patient's overall health.

Human tooth enamel naturally undergoes a process of demineralization. Exposure of enamel to saliva and food slowly leaches minerals from teeth and eventually leads to increased susceptibility to decay. This process of demineralization results in incipient caries which are typically very small defects in the enamel surface that are typically left untreated. Carious dentin demineralization also may occur in patients that have exposed regions of dentin resulting from decay below the cementum-enamel junction.

Demineralization eventually leads to cavitation of enamel coating such that there is exposure of the underlying tooth structure. Typically, this type of decay is treated by drilling out the decayed region and inserting a semi-permanent filling material. However, a less invasive means of arresting and reversing decay is desired.

There are currently numerous synthetic chemicals used in oral care products intended to treat or prevent tooth hypersensitivity, tooth decay, plaque build-up, gingivitis, periodontal disease and tooth demineralization. Although these synthetic chemicals may be effective, consumers desire more natural products to treat and prevent oral health issues, such as those stated above.

Current toothpastes have abrasives, fluorides, strong flavors to hide the unpleasant taste of some ingredients, thickeners to allow the toothpaste to stay on the toothbrush, detergents/surfactants to clean dirt off the teeth, and non-nutritive sweeteners so bacteria growth is not encouraged.

Many oral care formulations commonly contain personal care synthetic ingredients which include: colorants such as synthetic dyes; surfactants such as sodium lauryl sulfate (SLS); emulsion stabilizing agents and thickeners such as carbomers (synthetic polymers of acrylic acid); artificial sweeteners such as acesulfame, saccharine and aspartame; and artificial flavors.

In addition to numerous personal care synthetic ingredients, many oral care formulations may have natural ingredients that are synthetically-derived or processed. Processes such as ethoxylation, sulfination or polymerization have the potential to change the chemical make-up of ingredients that start out natural, but may not remain so after processing. These types of processes dilute or change the composition of an ingredient and can involve caustic solvents, impurities and leave residual compounds behind. Natural, ecological processes such as distillation, condensation, extraction, steamed distillation, pressure cooking and hydrolysis are desirable to maximize the purity of natural ingredients.

Because of a desire to use renewable resources and to eliminate contact with potentially harmful synthetic materials, natural-based oral care compositions are gaining increasing interest. Most of these oral care compositions contain only some natural ingredients with the majority of their components being synthetic. One difficulty in formulating all-natural oral care compositions is achieving acceptable consumer performance with a limited number of raw materials. The number of all-natural ingredients available is scarce when compared to the number of highly developed synthetic surfactants, emulsifiers, colorants and other synthetic ingredients. Furthermore, since natural ingredients are naturally derived from nature, the chemical makeup and stability is not contstant and can make formulating large batches, during different seasons, very challenging.

A particulate bioactive glass, calcium sodium phosphosilicate, was developed by NovaMin Technology, Inc (hereinafter "NovaMin® bioactive glass") and is used in dental care products. U.S. Pat. No. 5,735,942 describes NovaMin® bioactive glass in detail and is hereby incorporated by reference in its entirety. In aqueous solutions, NovaMin® bioactive glass comprises 45% SiO2, 24.5% Na2O, 24.5% CaO and 6% P2O5. NovaMin® bioactive glass delivers an ionic form of calcium, phosphorus, silica, and sodium which are necessary for bone and tooth mineralization. When microscopic particles of calcium sodium phosphosilicate are exposed to water, they release mineral ions that become available for the natural remineralization process. The ions form hydroxyapatite crystals, a form of hard and strong mineral in teeth. Calcium sodium phosphosilicate can be used as an effective, non-toxic alternative to fluoride or can be used in conjunction with fluoride.

Although manmade, calcium sodium phosphosilicate is a material that will form a layer of hydroxycarbonate apatite in vitro when placed in a simulated body fluid. NovaMin® bioactive glass is considered a class A bioactive material which will bond to both hard and soft tissue, so it provides an efficacious material for interaction with the tooth structure and does not trigger an overwhelmingly adverse immune response.

Prior art oral care and toothpaste compositions do not combine effective cleansing, demineralizing and plaque build-up reduction properties using almost exclusively naturally-derived, naturally-processed, GRAS (generally regarded as safe) ingredients. Prior art oral care and toothpaste compositions do not have at least 90% of the components of the product originating from renewable sources found in nature. Moreover, prior art oral care and toothpaste compositions do not have at least 90% of the components derived from natural, ecological processes. It is therefore an object of the present invention to provide an oral care and toothpaste composition that overcomes the disadvantages and shortcomings associated with those of the prior art.

SUMMARY OF THE INVENTION

In accordance with the above objects and those that will be mentioned and will become apparent below, disclosed herein is a natural, anhydrous oral care composition that cleanses, remineralizes and reduces plaque build-up on teeth when used as a toothpaste.

An aspect of the invention comprises a composition that contains an effective amount of a bioactive glass to remineralize teeth, a sweetening agent, a surface-cleansing agent, a phospholipid-containing material, a thickening agent, a pharmaceutically acceptable carrier, and optionally an effective amount of cranberry extract to inhibit the attachment of bacteria to the gums. The bioactive glass, sweetening agent, surface-cleansing agent, phospholipid-containing material, thickening agent, pharmaceutically acceptable carrier and cranberry extract are all naturally-derived, naturally-processed, GRAS ingredients.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in general.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage are in weight percent ("wt. %").

As used herein the term "bioactive glass" means a composition comprising particulate bioactive and biocompatible glass with the following constituents in the following weight percentages: $SiO_2$ 40-60%; CaO 10-30%; $NaO_2$ 10-35%; $P_2O_5$ 2-8%; $CaF_2$ 0-25%; $B_2O_3$ 0-10% and a particle size range less than 90 μm which includes an effective amount of dentin tubule occluding particles that are less than about 10 μm.

A green seal from the Natural Products Association (NPA), a trade organization that boasts about 10,000 members, aims to help consumers identify environmentally friendly options for their skin. Products carrying its natural seal for personal care products derive 95% of the ingredients from natural sources. According to the personal care NPA guidelines, natural applies to both the natural ingredients and the ecological processes used to create them. Several processes dilute or change the composition of an ingredient. Ethoxylation, sulfonation and polymerization processes are expressly excluded from the term "naturally-processed". For example, sulfonation uses harsh processing that involves sulfates, sulphonates and phosphates to create effective wetting agents for use in detergents and foaming agents. According to the NPA personal care guidelines, one example of a naturally derived synthetic substitute produced by processes such as sulfonation and ethoxylation is sodium lauryl/laureth sulfate (SLS). Thus, SLS is not an approved natural personal care ingredient. A list of NPA approved natural ingredients can be found in "Illustrative 'Positive List' of Ingredients A list of NPA approved natural processes can be found in "Natural Products Association Starndard and Certification for Personal Care Products".

The term "naturally-derived" as used herein means that the ingredient comes from or is made from a renewable resource found in nature (i.e., Flora, Fauna, Mineral). Petroleum compounds are expressly excluded from the term "naturally-derived".

The term "naturally-processed" as used herein means that the ingredients are processed using only ecologically-friendly processes. Ecologically-friendly processing is minimal processing that maximizes purity and minimizes negative effects on the ingredients. Non-limiting examples of natural processes include distillation, condensation, extraction, steamed distillation, pressure cooking and hydrolysis.

Other non-limiting examples of natural processes include: saponification which uses a strong alkali base (e.g., NaOH) to create a reaction with a fat or oil to produce soap, glycerine and water in one process; esterification and transesterification which involve reacting an alcohol and an acid or base to create safe emulsifiers, surfactants and solubalizers that thicken and hydrate moisturizers; and biofermentation which converts substances through the use of a yeast and/or a bacteria to produce nutrients and/or to purify formulations. The microorganisms do not survive the process.

The term "GRAS" has its ordinary meaning as used herein: generally recognized as safe by Food and Drug Administration (FDA) when used in accordance with FDA's good manufacturing practices (GMP) and contains no residues of heavy metals or other contaminants in excess of tolerances set by FDA or EPA The term "biodegradable" as used herein means microbial degradation of carbon containing materials. Biodegradable materials are tested under a recognized protocol and with tested methods of established regulatory bodies such as: EPA, EPA-TSCA, OECD, MITI or other similar or equivalent organizations in the US or internationally. Suitable non-limiting examples of test methods for biodegradation include: OECD methods in the 301-305 series. Generally, all biodegradable materials must meet the following limitations:

a) removal of dissolved organic carbon >70%
b) biological oxygen demand (BOD)>60%
c) % of BOD of theoretical oxygen demand >60%
d) % $CO_2$ evolution of theoretical >60%

The term "eco-friendly, natural composition" as used herein refers to compositions wherein at least 95% of the ingredients are naturally-derived, naturally-processed and GRAS.

The term "eco-friendly, natural ingredient" refers to an ingredient that is naturally-derived, naturally-processed and GRAS.

The oral care compositions disclosed herein contain at least 99% naturally-derived, naturally-processed, GRAS ingredients. Unlike prior art "natural" formulations, the compositions disclosed herein have been shown to be as good or better than their synthetic or quasi-synthetic counterparts.

FIG. 1 shows a cross-sectional diagram of a healthy tooth 10 showing the layers of the tooth and its internal structure, as well as how the tooth relates to the gum and surrounding jaw bone. The crown 12 is the part of the tooth that is visible above the gum (gingiva) 24. The neck 14 is the region of the tooth that is at the gum line, between the root and the crown. The root 16 is the region of the tooth that is below the gum. The number of roots per tooth will vary. Incisors and canine teeth have only one, whereas each molar and premolar has four roots per tooth. The crown of each tooth has a coating of enamel 18, which protects the underlying dentine 20.

Enamel is the hardest substance in the human body, harder even than bone. It gains its hardness from tightly packed rows of calcium and phosphorus crystals within a protein matrix structure, i.e., a crystalline latticework primarily composed of hydroxyapatite. Once the enamel has been formed during tooth development, there is little turnover of its minerals during life. Mature enamel is not considered to be a 'living' tissue. The major component of the inside of the tooth is dentine 20. Dentine is slightly softer than enamel, with a structure more like bone. It is elastic and compressible in contrast to the brittle nature of enamel. Dentine is a 'live' tissue. Dentine is sensitive and contains tiny tubules (not shown) throughout its structure that connect with the central nerve of the tooth within the pulp 22. Dentin tubules are approximately 1-2 µm in diameter with the dentin consisting of approximately 60% inorganic components and 40% organic composed mainly of collagen.

Below the gum 24, the dentine of the root is covered with a thin layer of cementum 26, rather than enamel. Cementum is a hard bone-like substance onto which the periodontal membrane 28 attaches. This membrane bonds the root of the tooth to the bone 30 of the jaw. It contains elastic fibers to allow some movement of the tooth within its bony socket.

Pulp 22 forms the central chamber of the tooth. The pulp is made of soft tissue and contains blood vessels to supply nutrients to the tooth, and nerves to enable the tooth to sense heat and cold. It also contains small lymph vessels which carry white blood cells to the tooth to help fight bacteria. The extension of the pulp within the root of the tooth is called the root canal 32. The root canal connects with the surrounding tissue via the opening at the tip of the root 34. Opening 34 is an opening in the cementum through which the tooth's nerve supply and blood supply enter the pulp from the surrounding tissue.

Hypersensitivity affects about 45 million adults in the United States and about 10 million are chronically affected with sensitive teeth. Tooth sensitivity is tooth discomfort after eating cold or hot foods or liquids or even breathing cold air. This problem often happens when gums recede and/or cementum is not presence. The gum tissue acts like a protective blanket to cover the roots of the teeth. Since they are not covered by hard enamel, as the gums recede the underlying tooth roots are exposed. Thousands of tiny dentinal tubules (channels) leading to the tooth's nerve center (pulp) are than exposed. These tubules allow more stimuli like heat, cold or pressure to reach the nerve in the tooth and cause pain. Over time, it is not uncommon for the gums to recede or the enamel or dentin on teeth to wear down, creating the condition of tooth sensitivity.

Plaque is mostly composed entirely of bacteria. Most oral bacteria is harmless but brushing your teeth 3 times a days can cut down the build up of bacteria that appears as plaque. When plaque stays on the teeth for a long time, they can turn acidic and eat away at the tooth's enamel. Also, eventually, plaque will harden and become tarter which is harder to remove.

Demineralization is the process of removing minerals, in the form of mineral ions, from dental enamel. Another way to describe demineralization is to say that some enamel has dissolved. As previously discussed, enamel is a crystalline latticework primarily composed of hydroxyapatite. A substantial number of mineral ions can be removed from the latticework without destroying its structural integrity; however, demineralized enamel transmits hot, cold, pressure and pain much more readily than normal enamel. When excessive demineralization occurs, the result is a cavity.

Demineralization is primarily caused by strong, stable acids which are found in acid foods, such as tomatoes or oranges. But, of greater concern, is the fact that these acids are also formed by oral bacteria. The bacteria feed on starches and sugars in the mouth, especially refined sugars, and secrete the acids as by-products. In nature, acids dissolve minerals, transforming them from solid mineral molecules into mineral ions that exist only in solution. Strong stable acids such as those secreted by oral bacteria do not break down easily, so very small quantities can continue to dissolve enamel, eventually resulting in a cavity.

Synthetic oral care products typically use sodium lauryl sulfate to help clean the teeth, provide a foam that helps to carry away debris, an anti-bacterial and anti-plaque agent and to enhance the effectiveness of fluoride; Carbomer (synthetic high molecular weight crosslinked polymers of acrylic acid) as a thickening agent; PEG 400 (polyethylene glycol 400 phosphate ester) to remove dirt on the teeth; and potassium acesulfame, saccharine and/or aspartame as a flavoring/sweetening agent.

One challenge associated with avoiding synthetic ingredients or methods is finding suitable eco-friendly, natural ingredients that provide textures, viscosities, creaminess, colors, flavors and fragrances that are equivalent to synthetic formulations. Far less ingredient options are available. Product stability and shelf life are particularly challenging aspects of the process. Eco-friendly, natural preservatives in products can be more delicate than synthetics and could possibly be more susceptible to break down with temperature changes during shipping. Thus, when synergistic interactions are discovered, they are embraced.

The ADA recommends the following proper tooth brushing technique: Place your toothbrush at a 45-degree angle against the gums. Move the brush back and forth gently in short (tooth-wide) strokes. Brush the outer tooth surfaces, the inner tooth surfaces, and the chewing surfaces of the teeth. Use the "toe" of the brush to clean the inside surfaces of the front teeth, using a gentle up-and-down stroke. Brush your tongue to remove bacteria and freshen your breath. The following can be found at the website http://www.ada.org/2624.aspx.

The key to healthy teeth is to (1) treat or prevent plaque build-up which can lead to tooth hypersensitivity, tooth decay, gingivitis, periodontal disease and tooth demineralization and (2) remineralize teeth where the enamel has been damaged due to the conditions discussed above.

Pharmaceutically Acceptable Carriers

The primary ingredient in most oral care compositions is an inert pharmaceutically acceptable carrier. The most common inert pharmaceutically acceptable carrier is water. However, compositions of the present invention must be anhydrous. Non-limiting examples of pharmaceutically acceptable carriers suitable for use with anhydrous compositions include sorbitol and glycerol. A preferred carrier is vegetable glycerin. Embodiments of the present invention can contain pharmaceutically acceptable carriers in amounts ranging from 40-70 percent by weight, and preferably 50-60 percent by weight.

Anhydrous compositions do not require a preservative, although a preservative could be included. Embodiments of the present invention are formulated to have shelf lives of at least 2 years and preferably at least 3 years.

Bioactive Glass

The occlusion of the dentinal tubules of a sensitive tooth results in reduction or elimination of the hypersensitivity. The duration of relief, however, is highly variable depending upon the method of occlusion. Many materials currently in use such as toothpastes containing strontium chloride and\or potassium nitrate provide short-lived relief. Fluoride has also been shown to partially fill dentinal tubules, but again the relief is short-lived. Hypersensitivity usually reappears because of tooth brush abrasion, presence of acid challenges in the mouth, or degradation of the coating material.

Bioactive glass chemically reacts with the surface of dentin and intimately bonds to a tooth's structure, creating a new mineral layer which leads to a significant reduction in the amount of sensitivity and significantly reducing the reopening of dentin tubules due to contact with oral fluids. The silica component of the bioactive glass composition chemically bonds to the dentin surface resulting in reduction of tooth hypersensitivity.

A consumer-desirable attribute of an oral care product is to provide a product having effective cleansing, demineralizing and plaque build-up reduction properties using almost exclusively natrually-derived, naturally-processed, GRAS ingredients. However, one obstacle to providing these benefits is that in order for the bioactive glass to be effective, it must be kept anhydrous so that it remains available to react with the saliva present in the mouth. Hence, finding the right combination to provide an anhydrous product is challenging on its own, and finding the right combination of eco-friendly, natural products presents an even greater challenge.

Several synthetic formulations that contain NovaMin® bioactive glass exist (e.g., Dr. Collins RESTORE® Remineralizing Toothpaste, Topex® ReNew™ Paste, NUPRO® NUSolutions™, SootheRx®, and Oravive™), but until now there has not been an effective eco-friendly, natural formulation.

Recently two important abstracts were presented to top clinical researchers and leading oral care manufacturers at the American Association of Dental Research indicating that NovaMin® bioactive glass containing fluoride varnishes and dentifrices not only have the potential to treat sensitivity (Abstract #1121—Fluoride, Calcium and Phosphorus Release from Novel NovaMin-Containing Fluoride Varnish: AADR Jounal of Dental Research 87 [Spec Iss A]: 1121, 2008 [www.dentalresearch.org]), but also have the potential to remineralize caries like lesions under both full and compromised salivary conditions (Abstract #0581—NovaMin+ Fluoride Dentifrice Re-Hardens [Remineralizes]Caries in Compromised Salivary Conditions In Vitro AADR Journal of Dental Research 87 [Spec Iss A]: 0581, 2008 [www.dental-research.org]). These new studies revealed further the NovaMin®bioactive glass anti-sensitivity benefits as well as the potential of NovaMin® the bioactive glass to enhance fluoride caries protection and efficacy.

The term "an effective amount of bioactive glass" as used herein means an amount which provides for at least partial occlusion of dentinal tubules. In one embodiment, the particulate bioactive and biocompatible glass have the following weight percentage: $SiO_2$ 40-60%; $CaO$ 10-30%; $Na_2O$ 10-35%; $P_2O_5$ 2-8%; $CaF_2$ 0-25%; $B_2O_3$ 0-10% and a particle size range less than 90 µm, alternatively less than 70 µm, alternatively less than 50 µm, which includes an effective amount of dentin tubule occluding particles that are less than about 10 µm, alternatively less than about 5 µm, alternatively less than about 2 µm. An effective amount of bioactive glass includes compositions that are between 5-8 percent by weight bioactive glass.

Cranberry Extract

According to the International & American Association for Dental Research, dental caries result from the interaction of specific bacteria with food constituents on tooth enamel. Dental plaque accumulation represents the first sign of this interaction. Dental plaque is a biofilm which is comprised of a population of bacteria growing on enamel that is enmeshed in a polysaccharide matrix. As the bacteria consume the sugars, an acid byproduct rapidly forms and its persistence results in dissolution of the tooth enamel.

Cranberries harbor a plethora of biological compounds such as flavonoids (e.g., quercetin and myricetin), phenolic acids (benzoic acid), anthocyanins, condensed tannins, among others. Research has shown that many of these substances can: (i) inhibit enzymes associated with the formation of the plaque polysaccharide matrix, (ii) block the adherence of bacteria to surfaces, (iii) prevent acid formation, and (iv) reduce acid tolerance of cariogenic organisms.

Because cranberry juice itself contains sugars, cranberry extracts are preferred for use in the oral care compositions disclosed herein. Studies have identified particular pronathocyanidins unique to the cranberry that inhibit the attachment of bacteria to the gums. For example, NutriCran®90 cranberry powder supplied by Decas Botanical Synergies, Carver, Mass. is suitable for use in the present invention. Compositions of the present invention can contain cranberry extracts, cranberry juice, cranberry juice powder or whole cranberry fruit powder in amounts ranging from 0.01-5 percent by weight, and preferably 0.5-3 percent by weight.

Surfactants, Thickeners and Emulsifying Agents

The most important constituents of an anhydrous toothpaste in relation to its mechanical cleansing properties are the abrasives and the surface active agents. In the compositions disclosed herein, surfactants and thickeners are used in conjunction with a pharmaceutically acceptable carrier to give toothpaste its overall texture and viscosity. Surfactants are used as cleansing or foaming agents.

Toothpaste works in tandem with a toothbrush to remove stains from the surface of teeth. Surfactants lower the surface tension of water so that bubbles are formed, creating the foaming action we associate with toothpastes. Foam keeps the toothpaste in the mouth and prevents it from dribbling out during the brushing process. A surfactant or cleansing agent is a substance that helps to remove food, debris and bacteria from the teeth and mouth by lowering the surface tension of the medium in which it is dissolved (saliva/water). An ideal toothpaste should foam effectively without causing irritation or damage to the gums or surrounding tissue. However, some synthetic surfactants, such as sodium lauryl sulfate, can also lead to irritation of the oral mucosa and have been linked to the promotion of canker sores (mouth ulcers) in susceptible individuals.

The compositions disclosed herein provide mild, eco-friendly, natural surfactants that provide foaming properties without potential irritation. Example surfactants include, for example, saponins (e.g., Quillaja and Yucca) and sodium cocoyl glutamate which is a mild natural surfactant, created from the amino acid L-Glutamic Acid & coconut fatty acids. It is very mild, hypo-allergenic, and biodegradable. Embodiments of the present invention can contain cleansing agent surfactants in amounts ranging between 0.1-3 percent by weight, with preferred amounts ranging between 0.1-1.5 percent by weight.

Typically surfactants are used as emulsifying agents. Embodiments of the present invention are anhydrous and therefore do not require an emulsifying agent. However, in some embodiments, an emulsifying agent, such as soy lecithin, could be added. Soy lecithin is extracted from soybean oil and contains three types of phospholipids; phosphatidylcholine (PC), phosphatidylethanolamine (PE) and phosphotidylinositol (PI) which are used to hold the anhydrous compositions together. Soy lecithin is multifunctional and helps promote solidity, giving a consistent texture as well as being compatible within an anhydrous environment. Embodiments of the present invention can contain soy lecithin or other similar substances in amounts ranging between 0.1-3 percent by weight, with preferred amounts ranging between 0.1-1.5 percent by weight.

Thickeners help to create the texture of toothpaste and can be used to adjust the viscosity. Carrageenan, cellulose gum, acacia gum and xanthan gum are common thickening agents. They prevent separation of the solid and liquid components, especially during storage. They also affect the speed and volume of foam production, the rate of flavor release and product dispersal, the appearance of the toothpaste ribbon on the toothbrush, and the rinsibility from the toothbrush. Embodiments of the present invention can contain thickeners in amounts ranging between 0.1-3 percent by weight, with preferred amounts ranging between 0.1-1.5 percent by weight.

Abrasives

Abrasives give toothpaste its cleaning power. Abrasives scrub and polish the outside of the teeth to get rid of stains, plaque and loosen particles on teeth. They also contribute to the degree of opacity of the paste or gel and may affect the paste's consistency, cost, and taste. Common abrasives include calcium phosphates, sodium bicarbonate (baking soda), alumina, calcium carbonate (chalk), and silica. Toothpaste should be abrasive enough to remove plaque and stains, but not abrasive enough to damage tooth enamel. A preferred abrasive for the compositions disclosed herein is silica. Embodiments of the present invention can contain abrasives in amounts ranging between 10-35 percent by weight, with preferred amounts ranging between 15-25 percent by weight.

Sweeteners and Flavoring Agents

Consumers consider flavor to be an important component of an oral care composition. Natural flavors such as berry (e.g., cranberry, strawberry, blueberry, etc. . . . ), citrus (e.g., orange, lemon, lime, etc. . . . ), tropical (e.g., banana, mango, papaya, etc. . . . ) mint (e.g., peppermint, spearmint, wintergreen, cinnamon, etc. . . . ), other herbal (e.g., bourbon, rye, anise, clove, caraway, coriander, eucalyptus, nutmeg, thyme, fennel, etc. . . . ) and combinations thereof are suitable for use in embodiments of the oral care formulations disclosed herein.

Aside from imparting particular flavors to a formulation, the use of sweeteners is important to make the oral care product palatable. Artificial sweeteners such as saccharin and aspartame are commonly used in toothpastes. Natural sweetener alternatives include *stevia rebaudiana*, maltodextrin, sorbitol and xylitol. The natural sweeteners can be used alone or may work synergistically in combination. Compositions disclosed herein can contain natural sweeteners and/or flavoring agents in amounts ranging between 0.1-20 percent by weight, with preferred amounts ranging between 0.1-15 percent by weight.

Xylitol is a white crystalline substance that looks and tastes like sugar. On food labels, xylitol is classified broadly as a carbohydrate and more narrowly as a polyol. Over 25 years of testing in widely different conditions confirm that xylitol is the best sweetener for teeth. Xylitol use reduces tooth decay rates both in high-risk groups (high caries prevalence, poor nutrition, and poor oral hygiene) and in low risk groups (low caries incidence using all current prevention recommendations). The human body produces up to 15 grams of xylitol from other food sources using established energy pathways. Thus, xylitol is not a strange or artificial substance, but a normal part of everyday metabolism. It is widely distributed throughout nature in small amounts. For example, some of the best sources are from fruits, berries, mushrooms lettuce, hardwoods, and corn cobs.

*Stevia Rebaudiana* is an herb in the Chrysanthemum family which grows wild as a small shrub in parts of Paraguay and Brazil. The glycosides in its leaves, including up to 10% stevioside, account for its incredible sweetness, making it unique among the nearly 300 species of *Stevia* plants. Two tests conducted by Purdue University's Dental Science Research Group have concluded that Stevioside is both fluoride compatible and "significantly" inhibits the development of plaque, thus *Stevia* may actually help to prevent cavities as well as improve the taste of oral care compositions. Thus, *stevia rebaudiana* extract is a desirable component in embodiments of the present invention.

Optional Ingredients

Embodiments of the present invention may contain the following optional ingredients: anticaries agents (e.g., sodium monoflurophosphate or disodium monofluorophosphate), preservatives, vitamins, plant extracts (e.g., *aloe barbadensis* leaf), colorants (e.g., titanium dioxide, mica), and any other ingredients generally known to those skilled in the art. For example, fluoride is probably the most commonly used anticaries agent used in oral care compositions. Embodiments of the present invention can contain optional ingredients in amounts ranging between 0-20 percent by weight, with preferred amounts ranging between 0.5-10 percent by weight.

EXAMPLES

Embodiments of the oral care compositions of the present invention are high performing, eco-friendly, natural formulations with a minimum of essential eco-friendly, natural ingredients. Competitive oral care composition products are either natural and inferior in performance or contain additional ingredients that make them non-natural, such as synthetic components. Embodiments of the present invention can have viscosities between 100,000-350,000 cps @ 25° C., RV T-bar E @ 5 rpm in 4 oz glass jar without guard leg. A preferred embodiment has a viscosity of 200,000 cps @ 25° C., RV T-bar E @ 5 rpm in 4 oz glass jar without guard leg.

Sample formulations of the present invention that contain fluoride include the following: (1) sodium monofluorophosphate 0.77% (0.14 w/v fluoride ion), glycerin, hydrated silica, xylitol, calcium sodium phosphosilicate, *vaccinium macrocarpon* (cranberry) fruit powder, *citrus aurantium dulcis* (orange) peel oil, tocopherol, beta-carotene, *chondrus crispus* (carrageenan), *stevia rebaudiana* extract, *acacia senegal* gum, xanthan gum, sodium ascorbate, silica, sodium cocoyl glutamate, maltodextrin, lecithin, mica, titanium dioxide, and cochineal; (ii) sodium monofluorophosphate 0.77% (0.14 w/v fluoride ion), glycerin, hydrated silica, xylitol, calcium sodium phosphosilicate, sodium cocoyl glutamate, titanium dioxide, *vaccinium macrocarpon* (cranberry) fruit powder, *chondrus crispus* (carrageenan), *stevia rebaudiana* extract, xanthan gum, silica, lecithin, maltodextrin and natural flavor; (iii) sodium monofluorophosphate 0.77% (0.14 w/v fluoride ion), glycerin, hydrated silica, xylitol, calcium sodium phosphosilicate, sodium cocoyl glutamate, titanium dioxide, *vaccinium macrocarpon* (cranberry) fruit powder, *stevia rebaudiana* extract, *chondrus crispus* (carrageenan), xanthan gum, silica, lecithin, maltodextrin and natural flavor; (iv) sodium monofluorophosphate 0.77% (0.14 w/v fluoride ion), glycerin, hydrated silica, xylitol, calcium sodium phosphosilicate, *chondrus crispus* (carrageenan), *vaccinium macrocarpon* (cranberry) fruit powder, silica, *stevia rebaudiana* extract, xanthan gum, sodium cocoyl glutamate, aroma (natural flavor), maltodextrin, CI 77019 (mica), and CI 77891 (titanium dioxide); and (v) sodium monofluorophosphate 0.77% (0.14 w/v fluoride ion), glycerin, hydrated silica, xylitol, calcium sodium phosphosilicate, *vaccinium macrocarpon* (cranberry) fruit powder, *stevia rebaudiana* extract, silica, *chondrus crispus* (carrageenan), aqua (water, eau), sodium cocoyl glutamate, aroma (natural flavor), maltodextrin, xanthan gum, CI 77891 (titanium dioxide), CI 75810 (chlorophyllin-copper complex), and CI 77019 (mica).

Sample formulations of the present invention that are fluoride-free include the following: (1) glycerin, hydrated silica, xylitol, calcium sodium phosphosilicate, *vaccinium macrocarpon* (cranberry) fruit powder, *aloe barbadensis* leaf powder, *chondrus crispus* (carrageenan), *stevia rebaudiana* extract, sodium cocoyl glutamate, xanthan gum, silica, lecithin, maltodextrin, mica, titanium dioxide, cochineal and natural flavor; (ii) glycerin, hydrated silica, xylitol, calcium sodium phosphosilicate, sodium cocoyl glutamate, titanium dioxide, *vaccinium macrocarpon* (cranberry) fruit powder, *aloe barbadensis* leaf powder, *chondrus crispus* (carrageenan), *stevia rebaudiana* extract, xanthan gum, silica, lecithin, maltodextrin and natural flavor; and (iii) glycerin, hydrated silica, xylitol, calcium sodium phosphosilicate, sodium cocoyl glutamate, titanium dioxide, *vaccinium macrocarpon* (cranberry) fruit powder, *aloe barbadensis* leaf powder, *stevia rebaudiana* extract, *chondrus crispus* (carrageenan), silica, xanthan gum, lecithin, maltodextrin and natural flavor.

Formulations A and B are example embodiments of the present invention.

| Formulation A |
|---|
| vegetable glycerin |
| hydrated silica |
| xylitol |
| calcium sodium phosphosilicate (bioactive glass) |
| sodium cocoyl glutamate |
| titanium dioxide |
| vaccinium macrocarpon (cranberry) fruit powder |
| stevia rebaudiana extract |
| chondrus crispus (carrageenan) |
| xanthan gum |
| silica |
| sodium monofluorophosphate 0.77% (0.14% w/v fluoride ion) |
| Lecithin |
| Maltodextrin |
| natural flavor |

Formulation A is a white-colored paste, with a viscosity of 100,000-350,000 cps @ 25° C., RV T-bar E @ 5 rpm in 4 oz glass jar without guard leg.

| Formulation B |
|---|
| vegetable glycerin |
| hydrated silica |
| xylitol |
| calcium sodium phosphosilicate (bioactive glass) |
| sodium cocoyl glutamate |
| titanium dioxide |
| vaccinium macrocarpon (cranberry) fruit powder |
| aloe barbadensis leaf powder |
| stevia rebaudiana extract |
| chondrus crispus (carrageenan) |
| xanthan gum |
| silica |
| lecithin |
| maltodextrin |
| natural flavor |

Formulation B is a white-colored paste, with a viscosity of 100,000-350,000 cps @ 25° C., RV T-bar E @ 5 rpm in 4 oz glass jar without guard leg.

Formulations A and B were compared to a commercially available "Natural" toothpaste, Formulation C, and a commercially available "Synthetic" toothpaste,

| Formulation C |
|---|
| water |
| glycerin |
| sodium lauryl sulfate |
| xylitol |
| chondrus crispus (carrageenan) |
| calcium carbonate |
| silica |
| sodium bicarbonate |
| zinc citrate trihydrate |
| spearmint/peppermint oil |

| Formulation D |
| --- |
| water |
| glycerin |
| tetrapotassium pyrophosphate |
| carbomer 956 |
| sodium lauryl sulfate |
| titanium dioxide |
| sodium saccharine |
| sorbitol |
| xanthan gum |
| silica |
| sodium monofluorohphosphate 0.76% (0.15% w/v fluoride ion) |

Formulation C is considered quasi-synthetic by the inventors because it contains sodium lauryl sulfate. Formulation D is considered synthetic because it contains sodium lauryl sulfate, tetrapotassium pyrophosphate, PEG-6, disodium pyrophospha and carbomer 956.

Two hundred to three hundred respondents between the ages of 21 and 64 were asked to evaluate numerous attributes of the four toothpaste formulations. The percentage of respondents that indicated they strongly agree or somewhat agree with the attribute statement listed are shown in Tabel 1. The natural formulations A and B achieved parity in many categories with the synthetic formulation and were generally preferred to the quasi-synthetic formulation.

TABLE 1

| Attribute | Formulation A | Formulation B | Formulation C | Formulation D |
| --- | --- | --- | --- | --- |
| Leaves teeth feeling clean and smooth | 87 | 86 | 77 | 93 |
| Provides fresh breath | 84 | 82 | 79 | 93 |
| Contains natural ingredients | 73 | 73 | 56 | 66 |
| Tastes good | 78 | 81 | 60 | 86 |
| Texture/Thickness of toothpaste was about right | 72 | 69 | 78 | 86 |
| Rinsed well from mouth | 81 | 77 | 70 | 92 |
| Amount of foam was about right | 79 | 72 | 75 | 85 |
| Color of toothpaste was about right | 88 | 89 | 89 | 92 |
| Left teeth feeling smooth | 89 | 87 | 81 | 96 |
| Left a pleasant after feel in the mouth | 39 | 43 | 36 | 54 |
| Liked the toothpaste overall | 80 | 80 | 66 | 92 |

A double blind study was conducted comparing the effectiveness on whitening and plaque of two adult toothpastes, Formulation A (described above) and a commercially available fluoride-containing toothpaste Formulation E.

| Formulation E |
| --- |
| water |
| glycerin |
| sodium lauryl sulfate |
| sodium saccharine |
| cellulose gum |
| tetrasodium pyrophosphate |
| dicalcium phosphate dehydrate |
| sodium monofluorophosphate 0.76% (0.15% w/v fluoride ion) |

The study evaluated 48 generally healthy male and female respondents between the ages of 25-75 for a one month period. The respondents were evaluated by a dentist who conducted an initial plaque examination and a shade determination. The respondents were instructed to use the supplied toothpaste and toothbrush twice daily as the only form of oral hygiene for the entire study period. The respondents received follow-up plaque examinations and shade determinations by the dentist after 2 and 4 weeks of product use.

Statistically significant decreases in plaque were observed after 2 and 4 weeks of independent use with both Formulation A and Formulation E. Likewise, statistically significant increases in teeth whitening were observed after 2 and 4 weeks of independent use with both Formulation A and Formulation E.

A double blind study was conducted comparing the effectiveness on whitening and plaque of two toothpastes recommended for children, Formulation F and Formulation E (from above).

| Formulation F |
| --- |
| vegetable glycerin |
| hydrated silica |
| xylitol |
| calcium sodium phosphosilicate (bioactive glass) |
| Sodium cocoyl glutamate |
| titanium dioxide |
| vaccinium macrocarpon (cranberry) fruit powder |
| aloe barbadensis leaf powder |
| stevia rebaudiana extract |
| chondrus crispus (carrageenan) |

-continued

| Formulation F |
| --- |
| xanthan gum |
| silica |
| lecithin |
| maltodextrin |
| natural flavor |
| mica |
| titanium dioxide |
| cochineal |

The study evaluated 49 generally healthy male and female respondents between the ages of 10-17 for a one month period. The respondents were evaluated by a dentist who conducted an initial plaque examination and a shade determination. The respondents were instructed to use the supplied toothpaste and toothbrush twice daily as the only form of oral hygiene for the entire study period. The respondents received follow-up plaque examinations and shade determinations by the dentist after 2 and 4 weeks of product use.

Statistically significant decreases in plaque were observed after 2 and 4 weeks of independent use with both Formulation F and Formulation E. Likewise, statistically significant increases in teeth whitening were observed after 2 and 4 weeks of independent use with both Formulation F and Formulation E.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A natural, anhydrous fluoride-containing toothpaste consisting essentially of:
   (a) an effective amount of calcium sodium phophosilicate;
   (b) sweetening agents comprising xylitol and *stevia rebaudiana*;
   (c) a cleansing agent surfactant comprising sodium cocoyl glutamate;
   (d) a phospholipid-containing material comprising soy lecithin;
   (e) thickening agents comprising carrageenan and xanthan gum;
   (f) an abrasive comprising silica;
   (g) an anti-plaque material comprising a cranberry extract;
   (h) a pharmaceutically acceptable carrier comprising vegetable glycerin; and
   (i) sodium monofluorophosphate;
   wherein (a)-(h) are naturally-derived, naturally-processed, and generally recognized as safe (GRAS);
   wherein the topical application of the toothpaste to human teeth cleanses, remineralizes and reduces plaque build-up on the teeth; and
   wherein the composition is anhydrous.

2. The natural, anhydrous toothpaste composition recited in claim 1, wherein
   the calcium sodium phosphosilicate is present in an amount ranging from 5-8 weight percent;
   the sweetening agents are present in total in an amount ranging from 0.1-20 weight percent;
   the cleansing agent surfactant is present in an amount ranging from 0.1-3 weight percent;
   the phospholipid-containing material is present in an amount ranging from 0.1-3 weight percent;
   the thickening agents are present in total in an amount ranging from 0.1-3 weight percent; and
   the pharmaceutically acceptable carrier is present in an amount ranging from 40-70 weight percent.

3. The natural, anhydrous toothpaste composition recited in claim 1, wherein the cranberry extract is present in an amount ranging from 0.1-5.0 weight percent.

4. The natural, anhydrous toothpaste composition recited in claim 1, wherein the toothpaste composition is shelf stable for at least 2 years.

5. The natural, anhydrous toothpaste composition recited in claim 4, wherein the toothpaste doesn't include a preservative.

6. The natural, anhydrous toothpaste composition recited in claim 1, wherein the viscosity of the composition is between 100,000 to 350,000 cps @ 25° C., RV T-bar E @ 5 rpm in 4 oz glass jar without guard leg.

7. The natural, anhydrous toothpaste composition recited in claim 1, wherein the viscosity of the composition is 200,000 cps @ 25° C., RV T-bar E @ 5 rpm in 4 oz glass jar without guard leg.

8. The natural, anhydrous toothpaste composition recited in claim 1, having a tooth whitening enhancement performance comparable to that of a synthetic formulation.

9. The natural, anhydrous toothpaste composition recited in claim 1, having a plaque reduction performance comparable to that of a synthetic formulation.

10. The natural, anhydrous toothpaste composition recited in claim 1, wherein the calcium sodium phophosilicate comprises 40-60 wt. % $SiO_2$; 10-30 wt. % CaO; 10-35 wt. % $Na_2O$; 2-8 wt. % $P_2P_5$; 0-25 wt. % $CaF_2$; 0-10 wt. % $B_2O_3$ and has a particle size less than 90 μm including an effective amount of dentin tubule occluding particles that are less than about 10 μm.

11. The natural, anhydrous toothpaste composition recited in claim 1, wherein, in aqueous solution, the calcium sodium phophosilicate is composed of 45 wt. % $SiO_2$ 24.5 wt. % $Na_2O$, 24.5 wt. % CaO and 6 wt. % $P_2O_5$.

12. A method for cleansing, remineralizing and reducing plaque build-up on human teeth comprising:
   providing a natural, anhydrous fluoride-containing toothpaste consisting essentially of (a) an effective amount of calcium sodium phophosilicate, (b) a sweetening agent comprising xylitol and *stevia rebaudiana*; (c) a cleansing agent surfactant comprising sodium cocoyl glutamate; (d) a phospholipid-containing material comprising soy lecithin; (e) thickening agents comprising carrageenan and xanthan gum; (f) an abrasive comprising silica; (g) an anti-plaque material comprising a cranberry extract; (h) a pharmaceutically acceptable carrier comprising vegetable glycerin; and (i) sodium monofluorophosphate; wherein (a)-(h) are naturally-derived, naturally-processed, and GRAS; and
   contacting human teeth with at least a pea-size amount of said toothpaste.

13. A method for cleansing, remineralizing and reducing plaque build-up on human teeth comprising:
   placing a natural, anhydrous fluoride-containing toothpaste consisting essentially of (a) an effective amount of calcium sodium phophosilicate, (b) sweetening agents comprising xylitol and *stevia rebaudiana*; (c) a cleansing agent surfactant comprising sodium cocoyl glutamate; (d) a phospholipid-containing material comprising soy lecithin; (e) thickening agents comprising carrageenan and xanthan gum; (f) an abrasive comprising silica; (g) an anti-plaque material comprising a cranberry extract; (h) a pharmaccutically acceptable carrier comprising vegetable glycerin; and (i) sodium monofluorophosphate; wherein (a)-(h) are naturally-derived, naturally-processed, and GRAS onto a toothbrush;
   using the toothpaste to brush human teeth in accordance with a tooth brushing procedure; and
   cleansing, remineralizing and reducing plaque build-up on said teeth.

* * * * *